United States Patent
LoCascio et al.

(10) Patent No.: US 7,095,959 B2
(45) Date of Patent: Aug. 22, 2006

(54) OPTICAL TIME DIVISION MULTIPLEXING/DEMULTIPLEXING SYSTEM

(75) Inventors: Michael LoCascio, Albany, NY (US); Clinton T. Ballinger, Burnt Hills, NY (US); Chester A. Pratt, Schenectady, NY (US); Daniel P. Landry, Clifton Park, NY (US)

(73) Assignee: Evident Technologies, Troy, NY (US)

( * ) Notice: Subject to any disclaimer, the term of this patent is extended or adjusted under 35 U.S.C. 154(b) by 846 days.

(21) Appl. No.: 09/883,992

(22) Filed: Jun. 20, 2001

(65) Prior Publication Data

US 2002/0196497 A1 Dec. 26, 2002

(51) Int. Cl.
*H04J 14/08* (2006.01)

(52) U.S. Cl. ............... 398/102; 398/75; 398/79; 398/98; 398/45; 398/161; 385/16; 385/5; 385/23; 385/39

(58) Field of Classification Search .............. 398/75, 398/79, 98, 45, 161, 175, 176, 102; 385/16, 385/5, 23, 39
See application file for complete search history.

(56) References Cited

U.S. PATENT DOCUMENTS

| 5,493,433 | A | | 2/1996 | Prucnal et al. ............ 359/123 |
| 5,535,032 | A | * | 7/1996 | Bottle ...................... 398/151 |
| 5,703,708 | A | * | 12/1997 | Das et al. .................. 398/102 |
| 6,178,022 | B1 | * | 1/2001 | Yoneyama ................ 398/182 |
| 6,262,823 | B1 | * | 7/2001 | Nowatzyk ................ 398/141 |
| 6,274,323 | B1 | | 8/2001 | Bruchez et al. ............ 435/6 |
| 6,323,983 | B1 | * | 11/2001 | Yamaguchi ............... 359/244 |

* cited by examiner

*Primary Examiner*—Hanh Phan
(74) *Attorney, Agent, or Firm*—Kenyon & Kenyon LLP (57) ABSTRACT

A multiplexing/demultiplexing system has a multiplexor that includes a first plurality of optical switches having a plurality of outputs and a first plurality of optical delay elements coupled to the optical switches. A source of optical light is coupled to the delay elements, and an optical combiner is coupled to the plurality of outputs and a source of framing pulses. A demultiplexor includes a first and second splitter, and a threshold detector coupled to the first splitter. The demultiplexor further includes a second plurality of optical delay elements coupled to the threshold detector, and a second plurality of optical switches coupled to the second splitter and the second plurality of delay elements.

37 Claims, 5 Drawing Sheets

OPTICAL TIME DIVISION MULTIPLEXING/DEMULTIPLEXING SYSTEM

CROSS-REFERENCES TO RELATED APPLICATIONS

This application is related to U.S. patent application Ser. No. 09/737,470, filed Dec. 18, 2000 and entitled "Optical Switch Having A Saturable Absorber".

FIELD OF THE INVENTION

The present invention is directed to optical communications. More particularly, the present invention is directed to an optical time division multiplexing/demultiplexing system.

BACKGROUND INFORMATION

Optical communication networks are rapidly being deployed to transmit both voice and data. Because the carrier frequencies used in optical fiber are orders of magnitude higher than used in any other communications medium, the bandwidth (i.e., data rate) afforded by such systems is inherently greater than twisted pair copper cables or coaxial cable.

Nevertheless, the majority of optical networks use electronic devices for signaling because electronic routing and signal processing devices are well developed. In some cases, sophisticated protocols requiring complex electronic logic are used.

Electronic processing requires converting an optical signal to the electronic domain prior to processing, then converting it back to the photonic domain for transmission. These conversions are time-consuming and a major bottleneck in optical networks.

All-optical switching technology, in which one optical signal is switched on or off upon signaling by an optical control beam, allows optical switching to be done without conversion, eliminating the optical-electrical-optical conversion bottleneck. Examples of such devices include Non-linear Optical Loop Mirrors and Semiconductor Optical Amplifier-based devices.

Another type of all-optical switch is a Quantum Dot Saturable Absorber switch, which is disclosed in U.S. patent application Ser. No. 09/737,470, filed Dec. 18, 2000 and entitled "Optical Switch Having A Saturable Absorber", the disclosure of which is herein incorporated by reference. The Quantum Dot Saturable Absorber switch operates by controlling the optical properties of a quantum dot material such as optical absorption or index of refraction with an external beam of light. It is much faster than conventional electronic devices, has low losses, and is well-suited for integration into larger-scale devices and systems.

A widely-used technique for transmitting and routing signals in optical communication networks is Time Division Multiplexing ("TDM"). This consists of dividing up a frame, or window in time, into multiple evenly-spaced time slots, and synchronously inserting a single bit of data from lower-bandwidth sources into a higher-bandwidth multiplexed stream. Recovering the signal consists of a demultiplexing operation in which the high-bandwidth stream is split into the individual low-bandwidth sources. The inherent simplicity of electronic TDM renders the processing logic and the devices required to be fairly straightforward and more easily implemented than complex protocols.

Optical time division multiplexing ("OTDM") is performed entirely optically without electronic conversion. Prior art OTDM implementations have encountered technological constraints that have prevented its implementation. For example, U.S. Pat. No. 5,493,433, entitled "Terahertz optical asymmetric demultiplexer" discloses an Optical Time Division Multiplexor system that includes a fiber loop that contains a nonlinear optical element placed asymmetrically within the loop. The entire device functions as an optical AND gate that allows an optical pulse to pass through when in the appropriate time slot. The device operates by first splitting the input signal pulses into two beams which are coupled to the optical fiber loop but travel in opposite directions around the loop. An optical control pulse is timed to alter the index of refraction of the nonlinear optical element so that a phase difference is generated between the counter-propagating optical signal pulses. When the optical signal pulses traverse the fiber loop they are coupled back together. If the pulses are in phase, constructive interference occurs and the pulses can exit the device. However, if the optical pulses are out of phase, deconstructive interference occurs and the optical signal cannot pass.

Optical loop type devices, such as disclosed in U.S. Pat. No. 5,493,433, are fairly fast (on the order of picoseconds) but are very power hungry and large. Therefore, these devices requires extremely expensive components and are difficult to integrate into more complex systems because of their large size. In addition, these types of devices are very sensitive to environmental factors such as temperature, because the refractive index of the fibers are related to temperature and because the length of fiber within the loop mirror is so long. Therefore, a small temperature change greatly alters the performance of the device.

Based on the foregoing, there is a need for an improved optical time division multiplexing/demultiplexing system.

SUMMARY OF THE INVENTION

One embodiment of the present invention is a multiplexor portion of a multiplexing/demultiplexing system. The multiplexor includes a first plurality of optical switches having a plurality of outputs and a first plurality of optical delay elements coupled to the optical switches. A source of optical light is coupled to the delay elements, and an optical combiner is coupled to the plurality of outputs and a source of framing pulses.

DETAILED DESCRIPTION

One embodiment of the present invention is an optical multiplexing/demultiplexing system that uses optical switches. The multiplexor combines or multiplexes lower data rate streams transmitted over independent optical fibers into a single, high data rate stream of data transmitted on a single optical fiber without converting the optical signal into an electrical form. The demultiplexor performs the opposite function.

Figure 1:
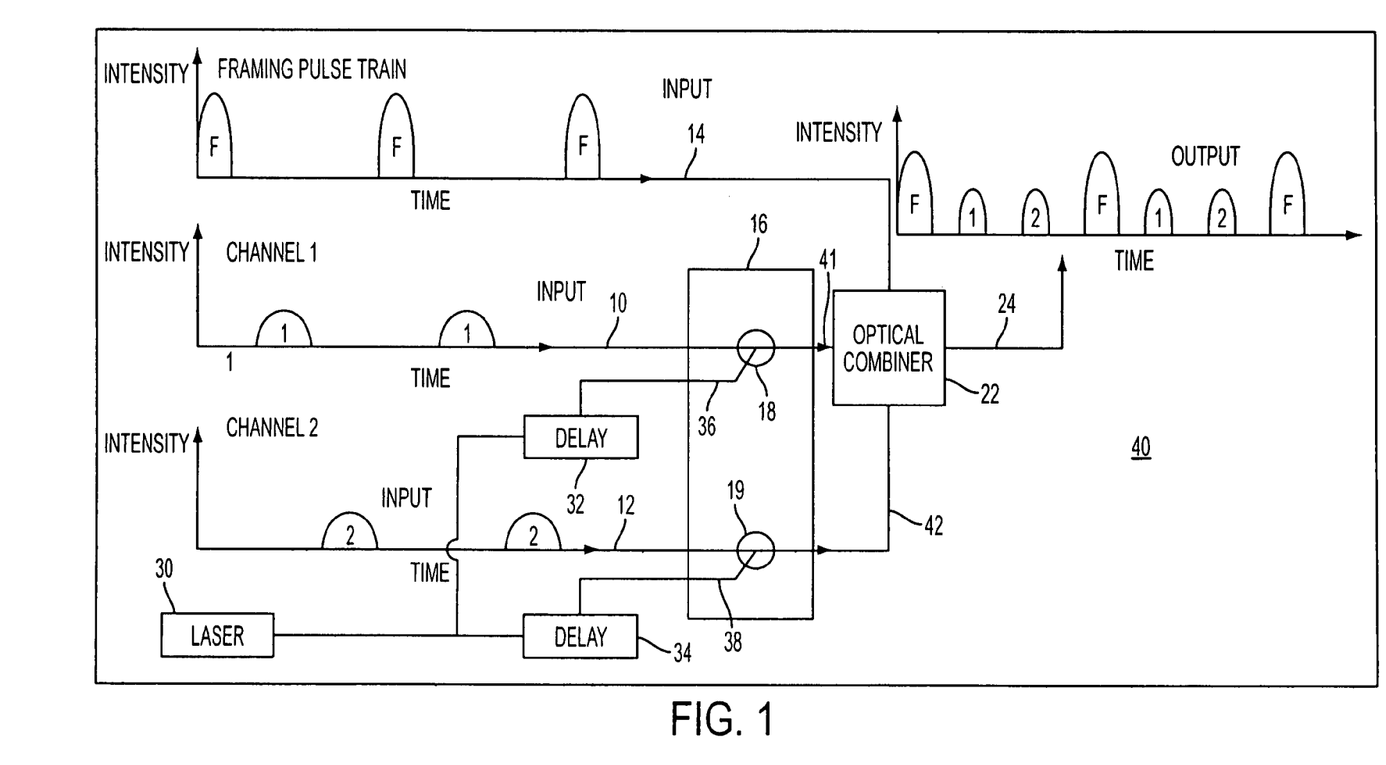
FIG. 1 is a block diagram of a multiplexor portion of the system in accordance with one embodiment of the present invention.

FIG. 1 is a block diagram of a multiplexor portion of the system in accordance with one embodiment of the present invention. Multiplexor 40 includes N number of input signal optical fibers 10 and 12, an input framing optical fiber 14 that transmits high intensity (relative to the input signal pulses) framing pulses, and an array 16 of N all-optical switches 18 and 19. Input pulses on input fibers 10 and 12 are positioned in their corresponding TDM slot.

Array 16 of all-optical switches is used to truncate the optical data pulses of the different channels on input optical fibers 10 and 12 to shorter pulse widths so a lower-data rate channel data can be multiplexed into higher-data rate multiplexed data. All-optical switches 18 and 19 within array 16 are designed to allow an input optical signal beam to be delivered to the output of the switch in the "on" state and to block the signal in the "off" state. All-optical switches 18 and 19 are controlled via high intensity optical beams called control optical beams at inputs 36 and 38, respectively. When the control beam is incident upon the switch, the switch is on. When the control optical beam is not illuminating the active region of the switch, the switch is off.

Each switch 18 and 19 within array 16 corresponds to one of input fibers 10 and 12. Array 16 is timed so that first switch 18 is "on" during the first time slot and "off" during the rest of the time slots, second switch 19 is "on" during the second time slot and "off" during the rest of the time slots, and so forth, for each switch in array 16. When all of the switches in array 16 have sequentially turned on and off, the sequence is repeated from the first switch to the last. The time period for the entire sequence is called the frame. At the beginning of each frame a pulse is added that has a higher intensity than the signal pulses. This pulse, called the framing pulse and transmitted on input framing optical fiber 14, indicates the beginning of the frame.

Multiplexor 40 further includes a laser 30 such as an amplified mode locked laser. Laser 30 has sufficient power to actuate all-optical switches 18 and 19 and implement the above-described switching sequence. Laser 30 generates a stream of intense equally timed optical pulses. The output of laser 30 is split into N optical time delay elements 32 and 34, each of which is coupled to a single all-optical switch 18 and 19. The difference in time delay resulting from time delay elements 32 and 34 is equal to the time slots that multiplexor 40 is set to. In one embodiment, time delay elements 32 and 34 consist of coils of optical fiber, the length of which determines the time required for the optical control pulse to travel through it. Coils having a longer length have longer delays because the optical pulses have to travel further.

All-optical switch array 16 is coupled to N optical output fibers 41 and 42 that are in turn coupled together into a single optical output fiber 24 via an optical combiner 22. Because the input signal pulses on input fibers 10 and 12 have been truncated to fit within specified time slots and are in sequence, the output of multiplexor 40 consists of N interleaved bits within a frame at an N times higher bit rate than the input data rates.

Figure 2:
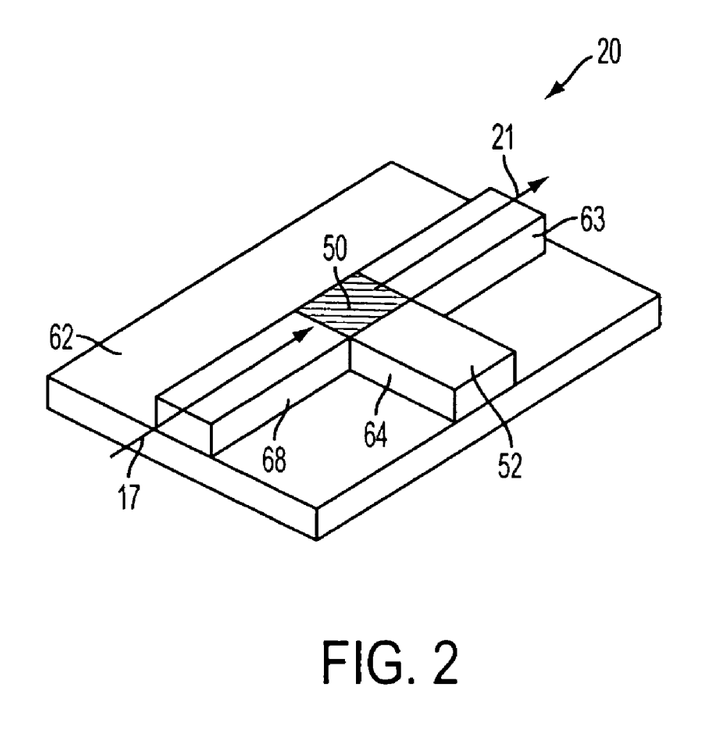
FIG. 2 is a perspective diagram of a saturable absorber switch in accordance with one embodiment of the present invention.

In one embodiment, optical switches 18 and 19 are saturable absorber switches. FIG. 2 is a perspective diagram of a saturable absorber switch in accordance with one embodiment of the present invention. Switch 20 includes a slab of saturable absorber material ("SA material") 50 formed on a substrate 62. Coupled to SA material 50, and also formed on substrate 62, is an input waveguide 68, a control beam waveguide 64 and an output waveguide 63. A control beam 52, such as control beams 36 and 38 from FIG. 1, is coupled to control beam waveguide 64, an input beam 17, such as inputs 10 and 12 from FIG. 1, is coupled to input waveguide 68, and output beam 21, such as output 24 from FIG. 1, is coupled to output waveguide 63.

SA material 50 is a non-linear absorbing medium. Under conditions where relatively low intensity light is incident upon SA material 50, it is highly absorbing. However, upon illumination by a high intensity beam, SA material 50 saturates, becoming less absorbing.

An incident optical beam having an associated wavelength within the absorption region of SA material 50 can saturate it (making it less absorbing) over its entire absorption range. Thus, it is possible for a high intensity optical beam (control beam 52) of wavelength $\lambda_1$ to switch another optical beam (input beam 17) having a wavelength $\lambda_2$ given that both wavelengths fall within the absorption band of SA material 50. Wavelength $\lambda_1$ can be either greater or smaller than wavelength $\lambda_2$. Therefore wavelength converter 10 can achieve both "up" conversion and "down" conversion functions, where "up" conversion refers to a conversion from a low energy photon (i.e., long wavelength photon) to a high energy photon (i.e. short wavelength photon) and "down" conversion refers to the opposite.

In general, a saturable absorber such as SA material 50 is a material that displays a reduction in the absorption coefficient at the operational wavelength with increased incident light intensity. The behavior of such a material can be modeled as a two state system, i.e., a system possessing two quantum states of different energies that an electron can exist in. In the natural state of the material, one in which no light is incident upon the material, all electrons lie in the lower energy state. An incident photon having a wavelength (hence energy) that corresponds to the energy difference between the quantum states will be absorbed if it excites an electron from the lower energy level to the upper energy level.

An electron in the upper state will drop back to the lower energy level in one of two ways. It can (1) spontaneously drop back and release energy as heat (referred to as "non-radiative recombination") or as a photon of the same wavelength that originally excited it (referred to as "spontaneous radiative recombination" or "spontaneous emission") or (2) interact with another photon, having the wavelength corresponding to the energy difference between quantum states, that forces the electron down to the lower energy level by the release of two photons (referred to as "spontaneous emission"). The average time the electron remains in the upper level (assuming the drop from the upper state to the lower state is by spontaneous recombination) is given by the relaxation constant ($\tau$).

At low light intensities there is a much higher probability of an electron being excited to an upper energy level than an electron being forced down to the lower energy level because at low light intensities very few electrons exist in the upper state. At higher light intensities a higher fraction of the electrons build up in the upper state. Because more electrons exist in the upper state there is a larger probability of an electron being forced to a lower energy level. At the limit (extremely high light intensities) an equal number of electrons exist in the upper state as in the lower state. At this point there is an equal probability of an electron in the lower energy levels jumping to the upper energy level (absorbing a photon) as an electron in the upper energy level interacting with a photon and dropping to the lower energy level releasing two photons. If both processes are considered there is no net reduction of the number of photons. Hence, the absorption falls to zero.

A saturable absorber such as SA material 50 differs from, for example, a non-linear material. As discussed, a saturable absorber involves the transitions of electrons between quantum states. In contrast, non-linear materials, instead of relying on transitions, involve the non-linear reaction due to the electric field of the photons at high photon fluxes (i.e., high light intensity). This reaction is called the electric polarization (P). Because a saturable absorber requires a transition between states, it is highly selective as to which wavelength it can operate in (i.e., only wavelengths that correspond to an electronic transition can saturate a saturable absorber).

One embodiment of SA material 50 is a composite material containing semiconductor nanocrystals (referred to as "quantum dots") contained in a glass or silicon matrix. The size, particle composition and coating of the quantum dots are such that there is high absorption in the desired wavelength region of the saturable absorber. In general, the absorption peak caused by the quantum dots is broadened over a range of wavelengths due to a distribution in the size of the quantum dots, thermal fluctuations, and broadening due to the uncertainty in the relaxation time.

Quantum dots interspersed within a matrix material offer an opportunity for an ideal saturable absorber for multiple reasons. For one, the quantum states of the quantum dots can be engineered to correspond to any wavelength simply by altering their size. Further, the density of quantum states (i.e., the number of electrons per unit volume that are able to jump from one quantum state to another) are much lower than in bulk semiconductor materials. Therefore, a lower intensity incident light beam is required for it to saturate. Further, quantum dots eliminate slower excitations that occur at high light intensities such as a two photon absorption that exists in bulk semiconductors. Therefore, the use of quantum dots enables a fast, low power (low intensity), and tunable saturable absorber.

In one embodiment, the quantum dots are comprised of Lead Sulfide, Lead Selenide, Indium Phosphide, Indium Arsenide, etc., and are approximately 6 nanometers in diameter. This size of the dots results in a large change of absorption intensity while maintaining fast switching speed. The intensity of light required to saturate the saturable absorber depends on the size and composition of the dots, as characterized by the optical cross section of the saturable absorber. The concentration of dots determines how thick a slab of material (quantum dots in glass) is required to produce a given change in intensity of the signal. In one embodiment, a thickness of 0.1 cm is required to arrive at a 20 dB signal change (assuming 50% saturation). Increasing the dot density allows the same change with a thinner device. The absorption length ($\alpha_0^{-1}$) is related to the optical cross section ($\sigma_0$) and the number density (dots per volume) of dots $N_d$ by:

$$\alpha_0 = N_d \sigma_0 \quad \text{Eq. 1}$$

A limitation exists to the concentration of dots within the matrix material because it is not possible to pack dots any closer than when they are touching. The densest packing configuration is the face-centered cubic ("FCC") lattice which has a packing density of 0.7.

In one embodiment, the quantum dots are produced in a glass matrix. The glass matrix material is beneficial because it is transparent to the light which is to be absorbed by the dots, and it acts to confine the electron-hole pairs because it has a much larger band gap than the quantum dot material. This quantum confinement allows the requisite absorption spectrum to be obtained. In other embodiments, the matrix material is a plastic, or a semiconductor that is transparent to the operational wavelengths. Other possible matrix materials include Silicate, Borosilicate, and Phosphosilicate glasses, Polymethyl methacrylate (PMMA), Acrylic, polyamine polymers, and semiconductors including Silicon, Silicon Carbide, Cadmium Sulphide, Cadmium Selenide, Cadmium Telluride, Zinc Sulphide, Aluminum Arsenide, Aluminum Phosphide and Gallium Arsenide.

In one embodiment, cladding is added to the quantum dots. The purpose of the cladding is to greatly increase the optical cross-section of the core semiconductor quantum dot, thus decreasing the optical power required for saturation as well as decreasing the relaxation time. An electrically conducting cladding material (like a metal) locally increases the light intensity within the core semiconductor, thus enhancing the absorption cross section. A semiconductor cladding material acts as a surface passivating agent and reduces the number of trapped states, which increases the absorption cross section.

The band-gap energy of the cladding material is wider than the band-gap of the core semiconductor. In one embodiment, wavelength converter 20 of FIG. 1 has an operational wavelength of 1500 nm (0.827 eV). In this embodiment, suitable semiconductor cladding materials include Silicon (Si), Silicon Carbide (SiC), Cadmium Sulfide (CdS), Cadmium Selenide (CdSe), Zinc Sulfide (ZnS), Zinc Selenide (ZnSe), Zinc Telluride (ZnTe), AIAs, AIP, AISb, GaAs and InP. In addition, other materials that include metals such as Ag, Au and Al are appropriate for use as cladding materials.

The thickness of the cladding coating determines the enhancement of the absorption coefficient of the quantum dot material. The parameter describing the coating thickness is the ratio of the core radius to the shell radius ("arat"). Typical values of arat are between 0.7 and 0.85. Thus for core radii between 2.5 nm and 5.0 nm (appropriate for PbS), a shell thickness between 0.5 nm and 2.5 nm gives the desired enhancement.

In one embodiment, the quantum dots are manufactured using a thermal precipitation process that involves dissolving some amount of semiconductor material in a molten glass. The melt is controllably cooled until the quantum dots begin to precipitate out in the form of nano-crystals. A method for manufacturing quantum dots using a thermal precipitation process is disclosed in, for example, P. T. Guerreiro et al., "PbS Quantum-Dot Doped Glasses as Saturable Absorbers for Mode Locking of a Cr:Forsterite Laser", Appl. Phys. Lett. 71 (12), Sep. 22, 1997 at 1595.

In another embodiment, SA material 50 of FIG. 2 is manufactured using a colloidal growth process that involves growing nano-crystal quantum dots in a solution. Specifically, semiconductor precursors are introduced into a heated surfactant solution. The precursors crack in the solution and the semiconductors combine to form the nano-crystals. The quantum dots can then be removed from the solution and combined with a powdered glass solution. The powdered glass, referred to as a "sol-gel" can be shaped into a variety of forms. The sol-gel can be sintered into a large block, drawn and sintered into a fiber, or spun on a substrate and sintered to form a thin film. A method for manufacturing quantum dots using a colloidal growth process is disclosed in, for example: (1) U.S. Pat. No. 5,505,928, entitled "Preparation of III–V Semiconductor Nanocrystals"; (2) Nozik et al., "Colloidal Quantum Dots of III–V Semiconductors", MRS Bulletin, February 1998 at 24; and (3) Hao et al., "Synthesis and Optical Properties of CdSe and CdSe/CdS Nanoparticles", Chem. Mater. 1999, 11 at 3096.

In other embodiments, optical switches 18 and 20 of FIG. 1 can be devices utilizing the Kerr effect, including Non-linear Optical Loop Mirrors or Mach-Zender interferometers, or utilizing the change in refractive index of pumped Semiconductor Optical Amplifiers in a Mach-Zender interferometer.

Figure 3:
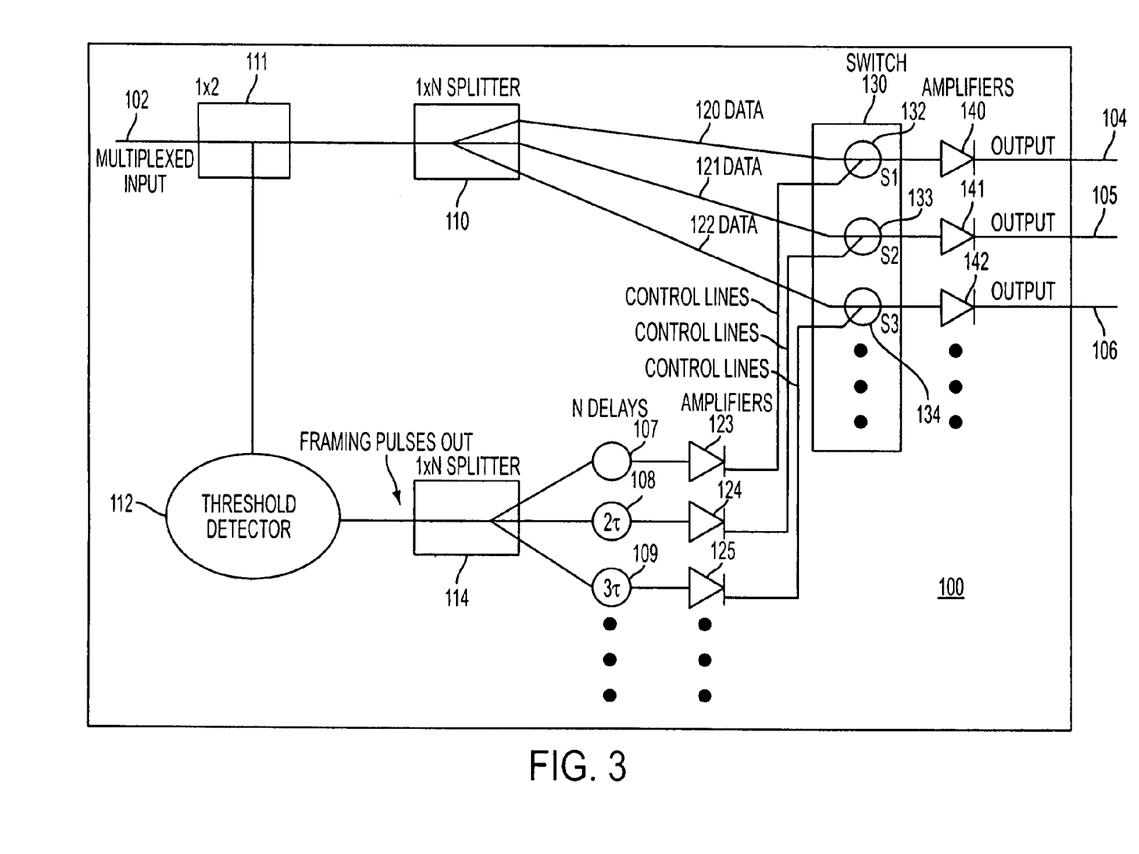
FIG. 3 is a block diagram of a demultiplexor portion of the system in accordance with one embodiment of the present invention.
Figure 4:
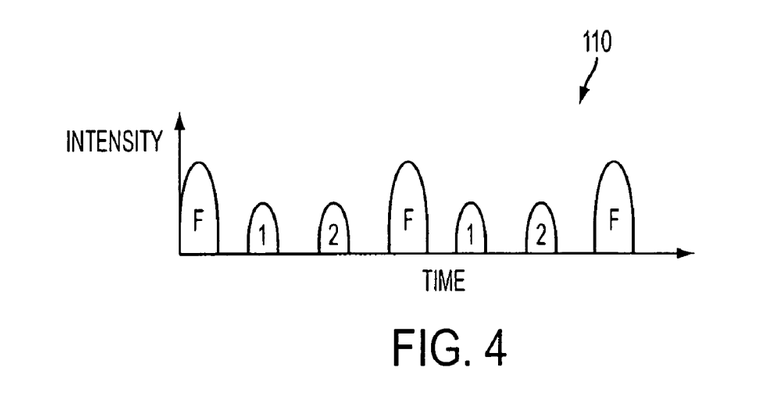
FIG. 4 is a graphical illustration of an input waveform of the demultiplexor portion of the system in accordance with one embodiment of the present invention.

FIG. 3 is a block diagram of a demultiplexor portion of the system in accordance with one embodiment of the present invention. Demultiplexor 100 splits or demultiplexes a single stream of data transmitted on a single optical fiber 102 into multiple streams of data outputted on multiple fibers 104–106. The input waveform transmitted on input optical fiber 102 has the same format as the output of multiplexor 40 and is illustrated in FIG. 4. Input waveform 110 includes frames consisting of a series of optical pulses comprising the data, preceded by a framing optical pulse having a higher intensity than that of the data pulses. Within the frame, each data pulse is to be transferred to an independent output line 104–106 of demultiplexor 100 after the demultiplexing operation, where the first data pulse is transferred to first output line, the second data pulse is transferred to the second output line, etc.

Demultiplexor 100 includes an optical splitting device 111 that divides the input signal into two signals, and an optical splitting device 110 that further divides the input optical signal into N signal beams 120–122 which are directed towards an all-optical switch array 130. Array 130 includes N all-optical switches 132–134. Each of the split signal beams of splitter 110 correspond to a single switch in array 130. One of the optical signal beams from optical splitting device 111 is directed towards a threshold detector 112.

Figure 5:
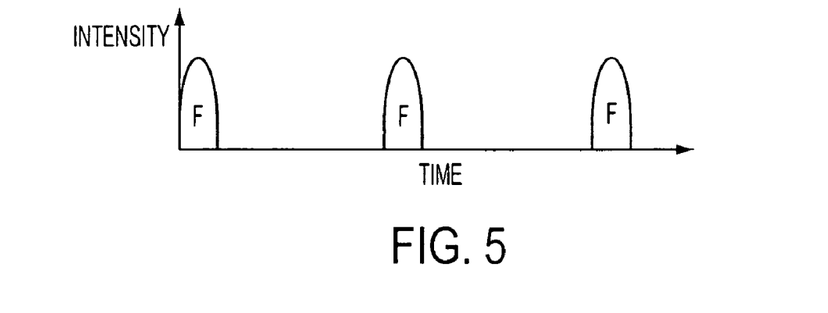
FIG. 5 is a graphical illustration of the input waveform after passing through a threshold detector of the demultiplexor portion.

All-optical threshold detector 112 is used to isolate the framing pulses from the data pulses in input 102. The framing pulses have much higher amplitude than the data pulses and are needed to define the beginning and end of the frame. In turn, the framing pulses define which subsequent data pulses are routed to which specific output. In one embodiment, threshold detector 112 includes a series of linear amplifiers and nonlinear absorbers, or vice versa, to isolate the larger amplitude framing pulses from the lower amplitude data pulses. FIG. 5 illustrates the waveform after passing through threshold detector 112. As shown, the data pulses have been removed leaving only the higher intensity framing pulses.

Following threshold detector 112 is a 1×N splitter 114 followed by N delay elements 107–109 and N amplifiers 123–125. Splitter 114, delay elements 107–109 and amplifiers 123–125 create optical pulses intense enough to actuate all-optical switches 132–134 (i.e., the control pulses) contained in switch array 130. Because there are N number of switches 132–134 within array 130 (each one corresponding to one of the data pulses), N control pulses are needed to actuate them, thus the need for 1×N optical splitter 114. Switches 132–134 are turned on, then off, in a time period equal to that of the data pulse, one after one another. Delay elements 107–109 are used to time the control pulses to achieve this.

The first output control pulse from amplifier 123 has a time delay $\tau$ that is equivalent to the time shift between data pulses, the second output control pulse from amplifier 124 has a $2\tau$ time delay, and the $N^{th}$ output has an $N\tau$ time delay. Each output of delay elements 107–109 corresponds to the control optical signal for an all-optical switch 132–134 in switching array 130. In general, a high intensity optical beam is required to actuate all-optical switches 132–134. Therefore, amplifiers 123–125 are used to amplify the N outputs of delay elements 107–109. In one embodiment, amplifiers 123–125 are Erbium Doped Fiber Amplifiers or Semiconductor Optical Amplifiers.

Figure 6:
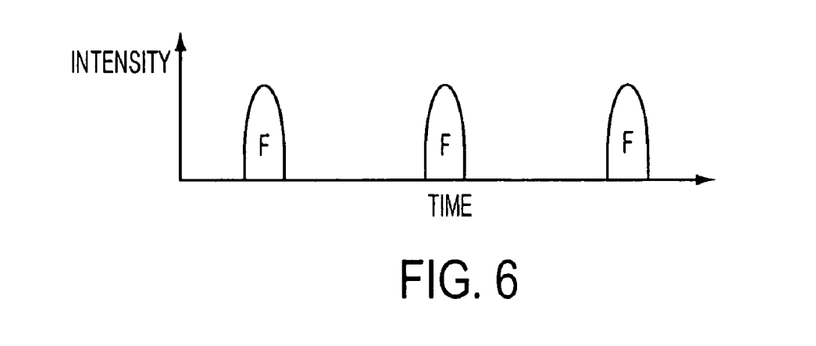
FIG. 6 is a graphical illustration of a resulting waveform output from a first delay element of the demultiplexor portion.

Delay elements 107–109 may be implemented using a section or cascade of sections of optical waveguide (i.e., optical fiber loops that delay the pulse by having travel over a linger distance before reaching the switch matrix). First delay element 107 only transmits light after a time duration approximately equal to the time duration of the first time slot. This has the effect of time-shifting the framing pulses by exactly one time slot. The resulting waveform output from first delay element 107 after 1×N splitter 114 and threshold detector 112 is shown in FIG. 6. As shown, the framing pulses have been shifted one time unit in comparison with FIG. 5, and now are aligned (in time) with the first optical data pulse.

Figure 7:
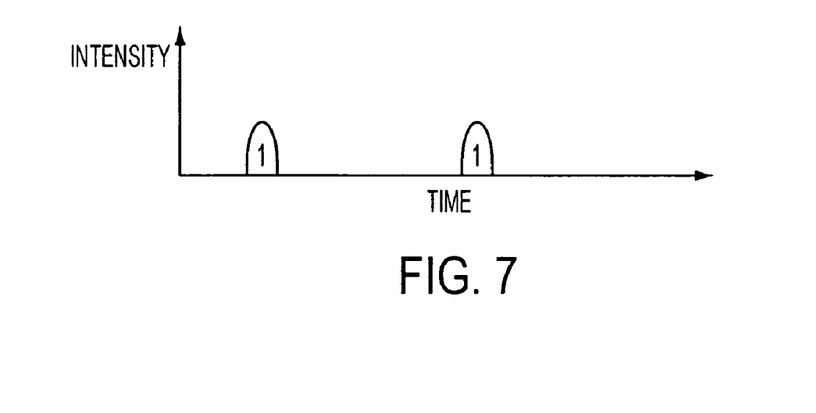
FIG. 7 illustrates an optical waveform at the output of the demultiplexor portion.

Switches 132–134 act as AND gates, in which an optical data pulse is transmitted through the switch when the switch is actuated by a control optical pulse output from amplifiers 123–125. Optical data pulses are not transmitted by the switch when it is not actuated by a control optical pulse. Each switch 132–134 is connected to one of N optical signal streams and one of N optical control streams and N output streams. Each switch 132–134 is turned on and then off in order, where first switch 132 is actuated first allowing only the first data pulse to be transmitted to a first output 104, second switch 133 is then turned on then off allowing only the second data pulse to be transmitted to a second output 105, and so forth, until all of the data pulses in the frame have been transmitted to separate outputs 104–106. Because the power of the data pulses is divided by N at 1×N splitter 110, each of the output signals may have to be amplified in an amplifier 140–142 in order to restore each of the outputted data pulses to the same amplitude as they were inputted. FIG. 7 illustrates the optical waveform at output 104.

As described, the multiplexing/demultiplexing system of the present invention uses all-optical switches to combine optical signals before transmission, and separating the original signals when the combined signal is received. The use of all-optical switches is more efficient that requiring optical signals to be converted to electrical signals.

Several embodiments of the present invention are specifically illustrated and/or described herein. However, it will be appreciated that modifications and variations of the present invention are covered by the above teachings and within the purview of the appended claims without departing from the spirit and intended scope of the invention.

What is claimed is:

1. A multiplexing/demultiplexing system comprising:
   a multiplexor comprising:
   a first plurality of optical switches having a plurality of inputs to receive optical pulses and having a plurality of outputs;
   a first plurality of optical delay elements coupled to and selectively actuating said optical switches;

a source of optical light coupled to said delay elements; and an optical combiner coupled to said plurality of outputs and a source of framing pulses.

2. The multiplexing/demultiplexing system of claim 1, further comprising:
a demultiplexor comprising:
a first splitter;
a second splitter coupled to said first splitter;
a threshold detector coupled to said first splitter;
a second plurality of optical delay elements coupled to said threshold detector; and
a second plurality of optical switches coupled to said second splitter and said second plurality of delay elements.

3. The multiplexing/demultiplexing system of claim 2, wherein said threshold detector detects the framing pulses.

4. The multiplexing/demultiplexing system of claim 2, wherein said second plurality of optical switches comprise a saturable absorber switch having a saturable absorber.

5. The multiplexing/demultiplexing system of claim 4, wherein said saturable absorber comprises quantum dots.

6. The multiplexing/demultiplexing system of claim 2, wherein a first delay element of said second plurality of optical delay elements has a first time delay of X, and a second delay element of said second plurality of optical delay elements has a second time delay of 2X.

7. The multiplexing/demultiplexing system of claim 2, further comprising a plurality of amplifiers coupled to said second plurality of optical delay elements.

8. The multiplexing/demultiplexing system of claim 1, wherein said first plurality of optical switches comprise a saturable absorber switch.

9. The multiplexing/demultiplexing system of claim 8, wherein said saturable absorber switch comprises a saturable absorber having quantum dots.

10. The multiplexing/demultiplexing system of claim 9, wherein said quantum dots are comprised of one or more of the group of Lead Sulfide, Lead Selenide, Indium Phosphide and Indium Arsenide.

11. The multiplexing/demultiplexing system of claim 9, wherein said saturable absorber comprises cladding coupled to said quantum dots.

12. The multiplexing/demultiplexing system of claim 9, wherein said quantum dots are manufactured using a colloidal growth process.

13. The multiplexing/demultiplexing system of claim 1, wherein said first plurality of optical switches comprise a Nonlinear Optical Loop Mirror.

14. The multiplexing/demultiplexing system of claim 1, wherein said first plurality of optical switches comprise a Mach-Zender interferometer.

15. The multiplexing/demultiplexing system of claim 1, wherein said source of optical light is a laser.

16. The multiplexing/demultiplexing system of claim 1, wherein said first plurality of optical switches have a plurality of control beam inputs, and said first plurality of optical delay elements are coupled to said control beam inputs.

17. The multiplexing/demultiplexing system of claim 1, wherein said multiplexor has a plurality of time slots, and said first plurality of optical delay elements have time differences substantially equal to said plurality of time slots.

18. An optical multiplexor comprising:
an optical switch array having a plurality of inputs to receive optical signal pulses and a plurality of outputs;
a plurality of delay elements coupled to and selectively actuating said switch array;
a laser coupled to said delay elements; and
an optical combiner coupled to said optical switch array outputs and having an input to receive optical framing pulses.

19. The multiplexor of claim 18, wherein said optical switch array comprises a plurality of saturable absorber optical switches.

20. The multiplexor of claim 19, wherein each of said saturable absorber switches comprises a saturable absorber having quantum dots.

21. The multiplexor of claim 20, wherein said quantum dots are comprised of one or more of the group of Lead Sulfide, Lead Selenide, Indium Phosphide and Indium Arsenide.

22. The multiplexor of claim 20, wherein said saturable absorber comprises cladding coupled to said quantum dots.

23. The multiplexor of claim 20, wherein said quantum dots are manufactured using a colloidal growth process.

24. The multiplexor of claim 20, wherein each of said saturable absorber switches comprises a control beam input, and said plurality of delay elements are coupled to said control beam input.

25. The multiplexor of claim 18, wherein said optical combiner generates a time division multiplexed output signal.

26. An optical demultiplexor comprising:
an optical switch array;
a first splitter having an input to receive a multiplexed optical signal;
a threshold detector coupled to said first splitter;
a second splitter coupled to said first splitter and said optical switch array;
a third splitter coupled to said threshold detector and said optical switch array.

27. The demultiplexor of claim 26, wherein said optical switch array comprises a plurality of saturable absorber optical switches.

28. The demultiplexor of claim 27, wherein each of said saturable absorber switches comprises a saturable absorber having quantum dots.

29. The demultiplexor of claim 28, wherein said quantum dots are comprised of one or more of the group of Lead Sulfide, Lead Selenide, Indium Phosphide and Indium Arsenide.

30. The demultiplexor of claim 28, wherein said saturable absorber comprises cladding coupled to said quantum dots.

31. The demultiplexor of claim 28, wherein said quantum dots are manufactured using a colloidal growth process.

32. The demultiplexor of claim 27, further comprising a plurality of delay elements coupled to said third splitter.

33. The demultiplexor of claim 32, wherein each of said saturable absorber switches comprises a control beam input, and said plurality of delay elements are coupled to said control beam input.

34. A method of multiplexing an optical signal comprising:
receiving a plurality of optical input signals;
receiving a framing pulse signal;
inputting each of said optical input signals to an input of a respective one of a plurality of optical switches;
providing a light source to a plurality of delay elements;
inputting an output of each of said delay elements to a control beam input of the respective one of the optical switches; and combining outputs of said plurality of switches with the framing pulse signal.

35. The method of claim 34, wherein said optical switches are saturable absorber switches.

36. A method of demultiplexing an optical signal comprising:
- receiving a multiplexed optical signal having framing pulses and data pulses;
- dividing the framing pulses from the data pulses;
- splitting the framing pulses;
- delaying at least one of the split framing pulses;
- inputting said split framing pulses to a control beam input of an optical switch; and
- inputting the data pulses to a switch input of the optical switch.

37. The method of claim 36, wherein said optical switch is a saturable absorber switch.

* * * * *

UNITED STATES PATENT AND TRADEMARK OFFICE
CERTIFICATE OF CORRECTION

PATENT NO. : 7,095,959 B2
APPLICATION NO. : 09/883992
DATED : August 22, 2006
INVENTOR(S) : Michael LoCascio et al.

It is certified that error appears in the above-identified patent and that said Letters Patent is hereby corrected as shown below:

Column 5, line 63, change "$(\alpha_o^{-1})$" to --$(\alpha_\Phi^{-1})$--;

Column 5, line 64, change "$(\sigma_o)$" to --$(\sigma_\Phi)$--;

Column 5, line 67, change "$\alpha_0 = N_d \alpha_o$" to --$\alpha_\Phi = N_d \alpha_\Phi$--;

Column 6, line 18, change "Sulphide" to --Sulfide--;

Column 6, line 19, change "Sulphide" to --Sulfide--;

Column 6, line 41, change "AI" to --A1--;

Column 7, line 9, change "1998 at 24" to --1998, Vol. 23 at 24--;

Column 7, line 14, change "Mach-Zender" to --Mach-Zehnder--; change "interferom-eters" to --interfero-meters--;

Column 7, line 16, change "Mach-Zender" to --Mach-Zehnder--;

Column 8, line 52, change "that" to --than--;

Column 9, line 53, change "Mach-Zender" to --Mach-Zehnder--;

Signed and Sealed this

Twenty-third Day of October, 2007

JON W. DUDAS
*Director of the United States Patent and Trademark Office*